US009616194B2

(12) United States Patent
Allum et al.

(10) Patent No.: US 9,616,194 B2
(45) Date of Patent: *Apr. 11, 2017

(54) VENTILATION MASK WITH INTEGRATED PILOTED EXHALATION VALVE AND METHOD OF VENTILATING A PATIENT USING THE SAME

(75) Inventors: Todd W. Allum, Livermore, CA (US); Joseph Cipollone, Mission Viejo, CA (US); George A. Kassanis, San Francisco, CA (US)

(73) Assignee: Breathe Technologies, Inc., Irvine, CA (US)

( * ) Notice: Subject to any disclaimer, the term of this patent is extended or adjusted under 35 U.S.C. 154(b) by 1315 days.

This patent is subject to a terminal disclaimer.

(21) Appl. No.: 13/431,827

(22) Filed: Mar. 27, 2012

(65) Prior Publication Data

US 2012/0325211 A1   Dec. 27, 2012
US 2013/0255684 A2   Oct. 3, 2013

Related U.S. Application Data

(60) Provisional application No. 61/499,950, filed on Jun. 22, 2011, provisional application No. 61/512,750, filed on Jul. 28, 2011.

(51) Int. Cl.
*A61M 16/06* (2006.01)
*A61M 16/00* (2006.01)
(Continued)

(52) U.S. Cl.
CPC ...... *A61M 16/208* (2013.01); *A61M 16/0003* (2014.02); *A61M 16/0622* (2014.02);
(Continued)

(58) Field of Classification Search
CPC . A61M 16/201; A61M 16/207; A61M 16/208
(Continued)

(56) References Cited

U.S. PATENT DOCUMENTS 8,413 A    10/1851  St. John
42,346 A    4/1864  Ghambeblin
(Continued)

FOREIGN PATENT DOCUMENTS

AU    2003217098 A1   12/2003
EP      1629859 A1    3/2006
(Continued)

OTHER PUBLICATIONS

Heat and Moisture Exchangers in Artificial Ventilation: An Experimental Study of the Effect of Gas Leakage S. E. Tilling and B. Hayes Br. J. Anaesth. (1987) 59(9): 1181-1188.
(Continued)

*Primary Examiner* — Tan-Uyen (Jackie) T Ho
*Assistant Examiner* — Joseph D Boecker
(74) *Attorney, Agent, or Firm* — Stetina Brunda Garred and Brucker; Mark Garred

(57) ABSTRACT

In accordance with the present invention, there is provided a mask for achieving positive pressure mechanical ventilation (inclusive of CPAP, ventilator support, critical care ventilation, emergency applications), and a method for a operating a ventilation system including such mask. The mask of the present invention includes a piloted exhalation valve that is used to achieve the target pressures/flows to the patient. The pilot for the valve may be pneumatic and driven from the gas supply tubing from the ventilator. The pilot may also be a preset pressure derived in the mask, a separate pneumatic line from the ventilator, or an electro-mechanical control. Additionally, the valve can be implemented with a diaphragm or with a flapper.

16 Claims, 4 Drawing Sheets

(51) Int. Cl.
    *A61M 16/20* (2006.01)
    *A61M 16/08* (2006.01)
    *A61M 16/10* (2006.01)

(52) U.S. Cl.
    CPC .... *A61M 16/0666* (2013.01); *A61M 16/0833* (2014.02); *A61M 16/0875* (2013.01); *A61M 16/1045* (2013.01); *A61M 16/201* (2014.02); *A61M 16/207* (2014.02); *A61M 2016/0027* (2013.01); *A61M 2205/3334* (2013.01)

(58) Field of Classification Search
    USPC .................. 128/204.21, 204.23, 205.24
    See application file for complete search history.

(56) References Cited

U.S. PATENT DOCUMENTS

| | | | |
|---|---|---|---|
| 53,694 A | 4/1866 | Smith | |
| 53,695 A | 4/1866 | Somes | |
| 189,153 A | 4/1877 | Towle et al. | |
| 252,515 A | 1/1882 | Ebdshaw | |
| 306,346 A | 10/1884 | Pabaf-Javal | |
| 321,600 A | 7/1885 | Heckee | |
| 416,701 A | 12/1889 | Yocom | |
| 430,380 A | 6/1890 | Evarts | |
| 432,325 A | 7/1890 | McIntyre | |
| 474,434 A | 5/1892 | Banker | |
| 516,494 A | 3/1894 | La Veck | |
| 539,217 A | 5/1895 | Chapman | |
| 546,673 A | 9/1895 | Meyer | |
| 3,326,214 A | 6/1967 | McCoy | |
| 3,675,649 A * | 7/1972 | Basham .................. | A62B 7/14 128/204.22 |
| 3,726,275 A | 4/1973 | Jackson et al. | |
| 3,802,431 A | 4/1974 | Farr | |
| 3,881,482 A | 5/1975 | Lindholm et al. | |
| 3,902,486 A | 9/1975 | Guichard | |
| 4,062,359 A | 12/1977 | Geaghan | |
| 4,121,583 A | 10/1978 | Chen | |
| 4,245,633 A | 1/1981 | Erceg | |
| 4,266,540 A | 5/1981 | Panzik et al. | |
| 4,278,082 A | 7/1981 | Blackmer | |
| 4,318,398 A | 3/1982 | Oetjen | |
| 4,325,365 A | 4/1982 | Barbuto | |
| 4,458,679 A | 7/1984 | Ward | |
| 4,535,767 A | 8/1985 | Tiep et al. | |
| 4,559,941 A | 12/1985 | Timmons et al. | |
| 4,572,177 A | 2/1986 | Tiep et al. | |
| 4,620,537 A | 11/1986 | Brown | |
| 694,089 A | 9/1987 | Brewer | |
| 4,699,139 A | 10/1987 | Marshall | |
| 4,739,757 A | 4/1988 | Edwards | |
| 4,771,770 A | 9/1988 | Artemenko et al. | |
| 4,787,105 A | 11/1988 | Phillips et al. | |
| 4,793,343 A | 12/1988 | Cummins et al. | |
| 4,836,200 A | 6/1989 | Clark et al. | |
| 4,873,972 A | 10/1989 | Magidson et al. | |
| 4,913,140 A | 4/1990 | Orec | |
| 4,949,733 A | 8/1990 | Sampson et al. | |
| D311,609 S | 10/1990 | Stoneburner | |
| 5,018,519 A | 5/1991 | Brown | |
| 5,025,805 A | 6/1991 | Nutter | |
| 5,062,145 A | 10/1991 | Zwaan et al. | |
| 5,065,756 A | 11/1991 | Rapoport | |
| 5,072,729 A | 12/1991 | DeVries | |
| 5,111,809 A | 5/1992 | Gamble et al. | |
| 5,117,820 A | 6/1992 | Robitaille | |
| 5,134,995 A | 8/1992 | Gruenke et al. | |
| 5,193,534 A | 3/1993 | Peppler | |
| 5,245,995 A | 9/1993 | Sullivan et al. | |
| 5,273,031 A * | 12/1993 | Olsson ................ | A61M 16/203 128/204.18 |
| 5,284,160 A | 2/1994 | Dryden | |
| 5,303,699 A | 4/1994 | Bonassa et al. | |
| 5,331,957 A | 7/1994 | Liu | |
| 5,353,788 A | 10/1994 | Miles et al. | |
| 5,367,604 A | 11/1994 | Murray | |
| 5,383,447 A | 1/1995 | Lang | |
| 5,400,776 A | 3/1995 | Bartholomew | |
| 5,433,192 A | 7/1995 | Ebeling | |
| 5,435,298 A | 7/1995 | Anthony | |
| 5,445,143 A | 8/1995 | Sims | |
| 5,462,048 A | 10/1995 | Lambert et al. | |
| 5,492,113 A | 2/1996 | Estes et al. | |
| 5,503,146 A | 4/1996 | Froehlich et al. | |
| 5,503,147 A | 4/1996 | Bertheau | |
| 5,505,768 A | 4/1996 | Altadonna | |
| 5,529,060 A | 6/1996 | Salmon et al. | |
| 5,537,996 A | 7/1996 | McPhee | |
| 5,537,997 A | 7/1996 | Mechlenburg et al. | |
| 5,542,416 A | 8/1996 | Chalvignac | |
| 5,546,930 A | 8/1996 | Wikefeldt | |
| 5,551,419 A | 9/1996 | Froehlich et al. | |
| 5,558,084 A | 9/1996 | Daniell et al. | |
| 5,586,551 A | 12/1996 | Hilliard | |
| 5,588,423 A | 12/1996 | Smith | |
| 5,595,173 A | 1/1997 | Dodd | |
| 5,598,837 A | 2/1997 | Sirianne et al. | |
| 5,598,838 A | 2/1997 | Servidio | |
| 5,617,913 A | 4/1997 | DeGregoria et al. | |
| 5,640,951 A | 6/1997 | Huddart et al. | |
| 5,645,049 A | 7/1997 | Foley | |
| 5,647,344 A | 7/1997 | Turnbull | |
| 5,655,522 A | 8/1997 | Mechlenburg et al. | |
| 5,666,950 A | 9/1997 | Smith | |
| 5,673,687 A | 10/1997 | Dobson et al. | |
| 5,685,296 A | 11/1997 | Zdrojkowski et al. | |
| 5,694,923 A | 12/1997 | Hete et al. | |
| 5,697,364 A * | 12/1997 | Chua .................... | A61M 16/00 128/204.18 |
| 5,701,891 A | 12/1997 | Groenke | |
| 5,704,916 A | 1/1998 | Byrd | |
| 5,709,204 A | 1/1998 | Lester | |
| 5,730,122 A | 3/1998 | Lurie | |
| 5,735,267 A | 4/1998 | Tobia | |
| 5,813,399 A | 9/1998 | Isaza et al. | |
| 5,836,303 A | 11/1998 | Hurst et al. | |
| 5,848,590 A | 12/1998 | Smith | |
| 5,853,884 A | 12/1998 | Nichols et al. | |
| 5,860,418 A | 1/1999 | Lundberg | |
| 5,937,855 A | 8/1999 | Zdrojkowski et al. | |
| 5,957,131 A | 9/1999 | Hutchinson et al. | |
| 5,964,219 A | 10/1999 | Pekka | |
| 6,006,748 A * | 12/1999 | Hollis ................ | A61M 16/208 128/204.18 |
| 6,014,890 A | 1/2000 | Breen | |
| 6,017,374 A | 1/2000 | Huxham | |
| 6,026,811 A | 2/2000 | Settle | |
| 6,050,260 A | 4/2000 | Daniell et al. | |
| 6,078,730 A | 6/2000 | Huddart et al. | |
| 6,095,135 A | 8/2000 | Clawson et al. | |
| 6,116,235 A | 9/2000 | Walters et al. | |
| 6,135,432 A | 10/2000 | Hebblewhite et al. | |
| 6,165,105 A | 12/2000 | Boutellier et al. | |
| 6,201,223 B1 | 3/2001 | Nitta | |
| 6,272,933 B1 | 8/2001 | Gradon et al. | |
| 6,305,372 B1 | 10/2001 | Servidio | |
| 6,308,706 B1 | 10/2001 | Lammers et al. | |
| 6,318,366 B1 | 11/2001 | Davenport | |
| 6,318,369 B1 | 11/2001 | Gregory | |
| 6,332,463 B1 | 12/2001 | Farrugia et al. | |
| 6,338,473 B1 | 1/2002 | Hebblewhite et al. | |
| 6,349,722 B1 | 2/2002 | Gradon et al. | |
| 6,363,930 B1 | 4/2002 | Clawson et al. | |
| 6,367,474 B1 | 4/2002 | Berthon-Jones | |
| 6,394,084 B1 | 5/2002 | Nitta | |
| 6,394,091 B1 | 5/2002 | Giorgini | |
| 6,397,841 B1 | 6/2002 | Kenyon | |
| 6,398,197 B1 | 6/2002 | Dickinson | |
| 6,425,395 B1 | 7/2002 | Brewer et al. | |
| 6,435,178 B1 | 8/2002 | Lin | |
| 6,439,231 B1 | 8/2002 | Fukunaga et al. | |
| 6,478,026 B1 | 11/2002 | Wood | |
| 6,505,624 B1 | 1/2003 | Campbell, Sr. | |

(56) References Cited

U.S. PATENT DOCUMENTS

| | | |
|---|---|---|
| 6,516,798 B1 | 2/2003 | Davies |
| 6,523,538 B1 | 2/2003 | Wikefeldt |
| 6,536,432 B2 | 3/2003 | Truschel |
| 6,536,436 B1 | 3/2003 | McGlothen |
| 6,543,449 B1 | 4/2003 | Woodring et al. |
| 6,550,476 B1 | 4/2003 | Ryder |
| 6,554,260 B1 | 4/2003 | Lipscombe et al. |
| 6,557,551 B2 | 5/2003 | Nitta |
| 6,561,193 B1 | 5/2003 | Noble |
| 6,571,794 B1 | 6/2003 | Hansen |
| 6,581,601 B2 | 6/2003 | Ziaee |
| 6,584,972 B2 | 7/2003 | McPhee |
| 6,584,977 B1 | 7/2003 | Serowski |
| 6,595,215 B2 | 7/2003 | Wood |
| 6,598,604 B1 | 7/2003 | Seakins |
| 6,629,531 B2 | 10/2003 | Gleason et al. |
| 6,662,802 B2 | 12/2003 | Smith |
| 6,668,828 B1 | 12/2003 | Figley et al. |
| 6,679,264 B1 | 1/2004 | Deem et al. |
| 6,679,265 B2 | 1/2004 | Strickland et al. |
| 6,694,974 B1 | 2/2004 | George-Gradon et al. |
| 6,733,556 B1 | 5/2004 | Luigi |
| 6,766,800 B2 | 7/2004 | Chu et al. |
| 6,772,758 B2 | 8/2004 | Lambert |
| 6,772,999 B2 | 8/2004 | Lipscombe et al. |
| 6,776,158 B1 | 8/2004 | Anderson et al. |
| 6,802,314 B2 | 10/2004 | McPhee |
| 6,805,120 B1 | 10/2004 | Jeffrey et al. |
| 6,807,966 B2 | 10/2004 | Wright |
| 6,817,361 B2 | 11/2004 | Berthon-Jones |
| 6,851,425 B2 | 2/2005 | Jaffre et al. |
| 6,863,069 B2 | 3/2005 | Wood |
| 6,886,562 B2 | 5/2005 | Ishizuka |
| 6,899,102 B1 | 5/2005 | McGlothen |
| 6,918,389 B2 | 7/2005 | Seakins et al. |
| 6,921,417 B2 | 7/2005 | Persson et al. |
| 6,923,181 B2 | 8/2005 | Tuck |
| 6,935,337 B2 | 8/2005 | Virr et al. |
| 6,953,354 B2 | 10/2005 | Edirisuriya |
| 6,976,488 B2 | 12/2005 | Halperin |
| 6,986,353 B2 | 1/2006 | Wright |
| 6,990,977 B1 | 1/2006 | Calluaud |
| 6,994,089 B2 | 2/2006 | Wood |
| 6,997,177 B2 | 2/2006 | Wood |
| 7,004,162 B1 | 2/2006 | Foley et al. |
| 7,013,361 B2 | 3/2006 | Liron |
| 7,032,592 B2 | 4/2006 | Castor |
| 7,043,979 B2 | 5/2006 | Smith |
| 7,047,974 B2 | 5/2006 | Strickland et al. |
| 7,051,733 B2 | 5/2006 | Gradon et al. |
| 7,069,928 B1 | 7/2006 | Waldo, Jr. |
| 7,086,399 B2 | 8/2006 | Makinson et al. |
| 7,106,955 B2 | 9/2006 | Thudor et al. |
| 7,111,624 B2 | 9/2006 | Thudor et al. |
| 7,120,354 B2 | 10/2006 | Mackie et al. |
| 7,137,388 B2 | 11/2006 | Virr et al. |
| 7,137,389 B2 | 11/2006 | Berthon-Jones |
| 7,140,367 B2 | 11/2006 | White |
| 7,146,976 B2 | 12/2006 | McKown |
| 7,146,979 B2 | 12/2006 | Seakins et al. |
| 7,188,624 B2 | 3/2007 | Wood |
| 7,192,550 B2 | 3/2007 | Berger et al. |
| 7,225,811 B2 | 6/2007 | Ruiz et al. |
| RE39,724 E | 7/2007 | Gradon et al. |
| 7,237,770 B2 | 7/2007 | Lipscombe et al. |
| 7,263,994 B2 | 9/2007 | Gradon et al. |
| 7,270,128 B2 | 9/2007 | Berthon-Jones |
| 7,305,988 B2 | 12/2007 | Acker et al. |
| 7,306,205 B2 | 12/2007 | Huddart et al. |
| 7,396,995 B2 | 7/2008 | Laurent et al. |
| 7,406,966 B2 | 8/2008 | Wondka |
| 7,428,902 B2 | 9/2008 | Du et al. |
| 7,438,073 B2 | 10/2008 | Delache et al. |
| 7,469,698 B1 | 12/2008 | Childers |
| 7,481,222 B2 | 1/2009 | Reissmann |
| 7,487,774 B2 | 2/2009 | Acker |
| 7,493,902 B2 | 2/2009 | White et al. |
| 7,506,647 B2 | 3/2009 | Worthington |
| 7,525,663 B2 | 4/2009 | Kwok et al. |
| RE40,806 E | 6/2009 | Gradon et al. |
| 7,549,419 B2 | 6/2009 | Carlsen et al. |
| 7,568,482 B2 | 8/2009 | Jaffre et al. |
| 7,588,029 B2 | 9/2009 | Smith et al. |
| 7,594,509 B2 | 9/2009 | Burk |
| 7,614,398 B2 | 11/2009 | Virr et al. |
| 7,616,871 B2 | 11/2009 | Kramer |
| 7,624,731 B2 | 12/2009 | Walstrom |
| 7,634,998 B1 | 12/2009 | Fenley |
| 7,658,189 B2 | 2/2010 | Davidson et al. |
| 7,708,017 B2 | 5/2010 | Davidson et al. |
| 7,717,113 B2 | 5/2010 | Andrieux |
| 7,770,579 B2 | 8/2010 | O'Connor et al. |
| 7,798,148 B2 | 9/2010 | Doshi et al. |
| 7,806,120 B2 | 10/2010 | Loomas et al. |
| 7,849,852 B2 | 12/2010 | Bremner et al. |
| 7,856,979 B2 | 12/2010 | Doshi et al. |
| 7,870,857 B2 | 1/2011 | Dhuper et al. |
| 7,913,497 B2 | 3/2011 | Dickerson |
| 7,913,640 B2 | 3/2011 | MacDonald et al. |
| 7,926,485 B2 | 4/2011 | Nguyen et al. |
| 7,942,148 B2 | 5/2011 | Davidson et al. |
| 7,958,891 B2 | 6/2011 | Smith et al. |
| 7,962,018 B2 | 6/2011 | Hunt et al. |
| 7,987,847 B2 | 8/2011 | Wickham et al. |
| 7,987,852 B2 | 8/2011 | Doshi et al. |
| 7,992,564 B2 | 8/2011 | Doshi et al. |
| 7,997,270 B2 | 8/2011 | Meier et al. |
| 8,006,691 B2 | 8/2011 | Kenyon et al. |
| 8,015,971 B2 | 9/2011 | Kwok |
| 8,020,551 B2 | 9/2011 | Virr et al. |
| RE42,843 E | 10/2011 | Strickland et al. |
| 8,028,693 B2 | 10/2011 | Trevor-Wilson et al. |
| 8,037,882 B2 | 10/2011 | Smith et al. |
| 8,042,535 B2 | 10/2011 | Kenyon et al. |
| 8,052,127 B2 | 11/2011 | Nichols et al. |
| 8,061,355 B2 | 11/2011 | Jaffre et al. |
| 8,061,357 B2 | 11/2011 | Pierce et al. |
| 8,069,854 B2 | 12/2011 | Colla et al. |
| 8,844,533 B2 * | 9/2014 | Allum ............... A61M 16/0666 128/205.24 |
| 2002/0083947 A1 | 7/2002 | Seakins |
| 2003/0079748 A1 | 5/2003 | Seakins |
| 2003/0079751 A1 | 5/2003 | Kwok |
| 2004/0035431 A1 | 2/2004 | Wright |
| 2004/0065327 A1 | 4/2004 | Gradon et al. |
| 2004/0211421 A1 | 10/2004 | Blansfield |
| 2005/0011521 A1 | 1/2005 | Sprinkle et al. |
| 2005/0121038 A1 | 6/2005 | Christopher |
| 2005/0126573 A1 | 6/2005 | Jaffre et al. |
| 2007/0056590 A1 | 3/2007 | Wolfson |
| 2007/0062534 A1 | 3/2007 | Fisher et al. |
| 2007/0079826 A1 | 4/2007 | Kramer et al. |
| 2007/0267023 A1 | 11/2007 | Ging et al. |
| 2007/0277825 A1 | 12/2007 | Bordewick et al. |
| 2008/0047560 A1 | 2/2008 | Veliss et al. |
| 2008/0060649 A1 | 3/2008 | Veliss et al. |
| 2008/0066745 A1 | 3/2008 | Janbakhsh et al. |
| 2008/0099013 A1 | 5/2008 | Graham |
| 2008/0105257 A1 | 5/2008 | Klasek et al. |
| 2008/0142015 A1 | 6/2008 | Groll |
| 2008/0156330 A1 | 7/2008 | Smith et al. |
| 2008/0190436 A1 | 8/2008 | Jaffe et al. |
| 2008/0223367 A1 | 9/2008 | Cox et al. |
| 2008/0257343 A1 | 10/2008 | Peterson |
| 2008/0302361 A1 | 12/2008 | Snow et al. |
| 2009/0000620 A1 | 1/2009 | Virr |
| 2009/0044808 A1 | 2/2009 | Guney et al. |
| 2009/0050153 A1 | 2/2009 | Brunner |
| 2009/0065005 A1 | 3/2009 | Ades |
| 2009/0065729 A1 | 3/2009 | Worboys et al. |
| 2009/0095295 A1 | 4/2009 | Wruck et al. |
| 2009/0114221 A1 | 5/2009 | Nagorny |
| 2009/0114229 A1 | 5/2009 | Frater et al. |
| 2009/0133700 A1 | 5/2009 | Martin et al. |

(56) References Cited

U.S. PATENT DOCUMENTS

| | | |
|---|---|---|
| 2009/0151719 A1 | 6/2009 | Wondka et al. |
| 2009/0151724 A1* | 6/2009 | Wondka ............ A61M 16/0096 128/204.23 |
| 2009/0151728 A1 | 6/2009 | McConnell et al. |
| 2009/0174092 A1 | 7/2009 | Kwok |
| 2009/0194106 A1 | 8/2009 | Smith et al. |
| 2009/0223514 A1 | 9/2009 | Smith et al. |
| 2009/0229606 A1 | 9/2009 | Tang et al. |
| 2009/0241948 A1 | 10/2009 | Clancy et al. |
| 2009/0247967 A1 | 10/2009 | Delli Paoli, Jr. |
| 2009/0277448 A1 | 11/2009 | Ahlmen et al. |
| 2009/0277452 A1 | 11/2009 | Lubke et al. |
| 2009/0293881 A1 | 12/2009 | Graham |
| 2009/0301478 A1 | 12/2009 | Ohmura et al. |
| 2009/0320840 A1 | 12/2009 | Klasek et al. |
| 2010/0018534 A1 | 1/2010 | Veliss et al. |
| 2010/0043796 A1 | 2/2010 | Meynink et al. |
| 2010/0071693 A1 | 3/2010 | Allum et al. |
| 2010/0078017 A1 | 4/2010 | Andrieux |
| 2010/0083965 A1 | 4/2010 | Virr et al. |
| 2010/0095966 A1 | 4/2010 | Dureus |
| 2010/0101575 A1 | 4/2010 | Fedorko et al. |
| 2010/0101584 A1 | 4/2010 | Bledstein et al. |
| 2010/0132717 A1 | 6/2010 | Davidson et al. |
| 2010/0147299 A1 | 6/2010 | Row et al. |
| 2010/0154796 A1 | 6/2010 | Smith et al. |
| 2010/0180895 A1 | 7/2010 | Kwok et al. |
| 2010/0206308 A1 | 8/2010 | Klasek et al. |
| 2010/0206312 A1 | 8/2010 | O'Leary |
| 2010/0236549 A1 | 9/2010 | Selvarajan et al. |
| 2010/0252037 A1* | 10/2010 | Wondka ............ A61M 16/0666 128/203.12 |
| 2010/0252039 A1 | 10/2010 | Cipollone et al. |
| 2010/0252040 A1 | 10/2010 | Kapust et al. |
| 2010/0252041 A1 | 10/2010 | Kapust et al. |
| 2010/0252042 A1 | 10/2010 | Kapust et al. |
| 2010/0282247 A1 | 11/2010 | Kadrichu et al. |
| 2011/0017212 A1 | 1/2011 | Kenyon et al. |
| 2011/0023874 A1 | 2/2011 | Bath et al. |
| 2011/0023877 A1 | 2/2011 | Kenyon et al. |
| 2011/0030691 A1 | 2/2011 | Campbell |
| 2011/0067704 A1 | 3/2011 | Kooij et al. |
| 2011/0073111 A1 | 3/2011 | Stone et al. |
| 2011/0094518 A1 | 4/2011 | Cipollone et al. |
| 2011/0108036 A1 | 5/2011 | Thomas |
| 2011/0120462 A1 | 5/2011 | Tatkov et al. |
| 2011/0126834 A1 | 6/2011 | Winter et al. |
| 2011/0126835 A1 | 6/2011 | Winter et al. |
| 2011/0162647 A1 | 7/2011 | Huby et al. |
| 2011/0197885 A1* | 8/2011 | Wondka et al. ......... 128/204.22 |
| 2011/0203595 A1 | 8/2011 | Hashemieh |
| 2011/0209709 A1 | 9/2011 | Davidson et al. |
| 2011/0214676 A1 | 9/2011 | Allum et al. |
| 2011/0247619 A1 | 10/2011 | Formica et al. |
| 2011/0253136 A1 | 10/2011 | Sweeney et al. |
| 2011/0253147 A1* | 10/2011 | Gusky ................... A61M 16/06 128/207.18 |
| 2011/0265796 A1 | 11/2011 | Amarasinghe et al. |
| 2011/0283999 A2 | 11/2011 | Smith et al. |
| 2011/0297150 A1 | 12/2011 | Kwok |
| 2012/0060837 A1* | 3/2012 | Liu ................... A61M 16/0051 128/204.21 |
| 2012/0330183 A1* | 12/2012 | Allum ............... A61M 16/0666 600/561 |
| 2014/0000610 A1* | 1/2014 | Rapoport .......... A61M 16/0666 128/204.23 |

FOREIGN PATENT DOCUMENTS

| | | |
|---|---|---|
| EP | 2269681 A2 | 1/2011 |
| WO | 0195965 A1 | 12/2001 |
| WO | 2009109005 A1 | 9/2009 |
| WO | 2010076704 A1 | 7/2010 |
| WO | 2011029074 A1 | 3/2011 |

OTHER PUBLICATIONS

PCT Search Report and Written Opinion for PCT/US2012/43006, issued Oct. 23, 2012.

PCT Search Report and Written Opinion for PCT/US2012/43011, issued Sep. 25, 2012.

Extended European Search Report mailed May 28, 2015 for European Patent Application No. EP 12 80 2913.

\* cited by examiner

VENTILATION MASK WITH INTEGRATED PILOTED EXHALATION VALVE AND METHOD OF VENTILATING A PATIENT USING THE SAME

CROSS-REFERENCE TO RELATED APPLICATIONS

The present application claims priority to U.S. Provisional Patent Application Ser. No. 61/499,950 entitled VENTILATION MASK WITH INTEGRATED PILOTED EXHALATION VALVE filed Jun. 22, 2011, and U.S. Provisional Patent Application Ser. No. 61/512,750 entitled VENTILATION MASK WITH INTEGRATED PILOTED EXHALATION VALVE AND METHOD OF VENTILATING A PATIENT USING THE SAME filed Jul. 28, 2011

STATEMENT RE: FEDERALLY SPONSORED RESEARCH/DEVELOPMENT

Not Applicable

BACKGROUND OF THE INVENTION

1. Field of the Invention

The present invention relates to systems and methods for controlling delivery of a pressurized flow of breathable gas to a patient and, more particularly, to a ventilation mask such as a nasal mask, nasal prongs mask or nasal pillows mask for use in critical care ventilation, respiratory insufficiency or PAP (Positive Airway Pressure) therapy and incorporating a piloted exhalation valve inside the mask.

2. Description of the Related Art

As is known in the medical arts, mechanical ventilators comprise medical devices that either perform or supplement breathing for patients. Early ventilators, such as the "iron lung", created negative pressure around the patient's chest to cause a flow of ambient air through the patient's nose and/or mouth into their lungs. However, the vast majority of contemporary ventilators instead use positive pressure to deliver gas to the patient's lungs via a patient circuit between the ventilator and the patient. The patient circuit typically consists of one or two large bore tubes (e.g., 22 mm ID for adults; 15 mm ID for pediatric) that interface to the ventilator on one end and a patient mask on the other end. Most often, the patient mask is not provided as part of the ventilator system, and a wide variety of patient masks can be used with any ventilator. The interfaces between the ventilator, patient circuit and patient masks are standardized as generic 15 mm/22 mm conical connectors, the size and shape of which are specified by regulatory bodies to assure interoperability.

Current ventilators are designed to support either single limb or dual limb patient circuits. Ventilators using single limb patient circuit are most typically used for less acute clinical requirements, such as treatment of obstructive sleep apnea or respiratory insufficiency. Ventilators using dual limb patient circuits are most typically used for critical care applications.

Single limb patient circuits are used only to carry gas flow from the ventilator to the patient and patient mask, and require a patient mask with vent holes. The pressure/flow characteristics of the vent holes in the mask are maintained according to standards that assure interoperability of masks with a multitude of ventilators that follow the standard. When utilizing single limb circuits, the patient inspires fresh gas from the patient circuit, and expires $CO_2$-enriched gas, which is purged from the system through the vent holes in the mask and partially breathed down the tube to the ventilator and re-breathed during the next breath. This constant purging of flow through vent holes in the mask when using single-limb circuits provides several disadvantages: 1) it requires the ventilator to provide significantly more flow than the patient requires, adding cost/complexity to the ventilator and requiring larger tubing; 2) the constant flow through the vent holes creates noise, which has proven to be a significant detriment to patients with sleep apnea that are trying to sleep with the mask, and also to their sleep partners; 3) the additional flow coming into proximity of the patient's nose and then exiting the system often causes dryness in the patient, which often drives the need for adding humidification to the system; and 4) patient-expired $CO_2$ flows partially out of the vent holes in the mask and partially into the patient circuit tubing, requiring a minimum flow through the tubing at all times in order to flush the $CO_2$. To address the problem of undesirable flow of patient-expired $CO_2$ back into the patient circuit tubing, currently known CPAP systems typically have a minimum-required pressure of 4 $cmH_2O$ whenever the patient is wearing the mask, which produces significant discomfort, claustrophobia and/or feeling of suffocation to early CPAP users and leads to a high (approximately 50%) non-compliance rate with CPAP therapy.

When utilizing dual limb circuits, the patient inspires fresh gas from one limb (the "inspiratory limb") of the patient circuit and expires $CO_2$-enriched gas from the second limb (the "expiratory limb") of the patient circuit. Both limbs of the dual limb patient circuit are connected together in a "Y" proximal to the patient to allow a single 15 mm or 22 mm conical connection to the patient mask.

In the patient circuits described above, the ventilator pressurizes the gas to be delivered to the patient inside the ventilator to the intended patient pressure, and then delivers that pressure to the patient through the patient circuit. Very small pressure drops develop through the patient circuit, typically around 1 $cmH_2O$, due to gas flow though the small amount of resistance created by the 22 mm or 15 mm ID tubing. Some ventilators compensate for this small pressure either by mathematical algorithms, or by sensing the tubing pressure more proximal to the patient.

Ventilators that utilize a dual limb patient circuit typically include an exhalation valve at the end of the expiratory limb proximal to the ventilator. The ventilator controls the exhalation valve, closes it during inspiration, and opens it during exhalation. Less sophisticated ventilators have binary control of the exhalation valve, in that they can control it to be either open or closed. More sophisticated ventilators are able to control the exhalation valve in an analog fashion, allowing them to control the pressure within the patient circuit by incrementally opening or closing the valve. Valves that support this incremental control are referred to as active exhalation valves. In existing ventilation systems, active exhalation valves are most typically implemented physically within the ventilator, and the remaining few ventilation systems with active exhalation valves locate the active exhalation valve within the patient circuit proximal to the ventilator. Active exhalation valves inside ventilators are typically actuated via an electromagnetic coil in the valve, whereas active exhalation valves in the patient circuit are typically pneumatically piloted from the ventilator.

BRIEF SUMMARY OF THE INVENTION

In accordance with the present invention, there is provided a mask for achieving positive pressure mechanical ventilation (inclusive of PAP, ventilatory support, critical care ventilation, emergency applications), and a method for a operating a ventilation system including such mask. The mask may include a pressure sensing modality proximal to the patient connection. Such pressure sensing modality may be a pneumatic port with tubing that allows transmission of the patient pressure back to the ventilator for measurement, or may include a transducer within the mask. The pressure sensing port, if included in the mask, is used in the system to allow pressure sensing for achieving and/or monitoring the therapeutic pressures. Alternately or additionally, the mask may include a flow sensing modality located therewithin for achieving and/or monitoring the patient and/or therapeutic flows.

The mask of the present invention also includes a piloted exhalation valve that is used to achieve the target pressures/flows to the patient. In the preferred embodiment, the pilot for the valve is pneumatic and driven from the gas supply tubing from the ventilator. The pilot can also be a preset pressure derived in the mask, a separate pneumatic line from the ventilator, or an electro-mechanical control. In accordance with the present invention, the valve can be implemented with a diaphragm or with a flapper.

One of the primary benefits attendant to including the valve inside the mask is that it provides a path for patient-expired $CO_2$ to exit the system without the need for a dual-limb patient circuit, and without the disadvantages associated with traditional single-limb patient circuits. For instance, in applications treating patients with sleep apnea, having the valve inside the mask allows patients to fall asleep while wearing the mask without the treatment pressure turned on, thereby preventing patient discomfort typically experienced with falling asleep while breathing at a positive pressure. In accordance with the present invention, the sensing described above may be used to sense a predetermined event, such as a set time, the detection of an event indicating patient airway obstruction, or the detection of a patient falling asleep, and start the positive airway pressure therapy upon sensing any such event, unlike existing devices which attempt to alleviate patient discomfort by starting at a lower pressure level (typically 4 cmH2O) and ramping the pressure up to a therapeutic level over a period of time. Additionally, having a valve inside the mask mitigates the need to have vent holes within the patient mask (a typical feature of mask used for sleep apnea) coincident with a purge flow to bleed patient expired $CO_2$ from the system. Alleviating the mask vent holes and associated extra flow of gas through the mask helps reduce noise generated by the mask, reduce $CO_2$ re-breathing, reduce patient nose dryness cause by excess gas flowing past the patient, and reduce flow requirements of the ventilator. Yet another benefit of the mask without vent holes and having the valve inside the same is that because there is not a constant flow through the mask and out of any vent holes, a heat moisture exchanger can also be incorporated into the mask, allowing a simple method of providing heated and humidified gas to the patient.

Another benefit for having the valve inside the mask is that it allows for a significant reduction in the tubing size, as it supports the ventilator delivering higher pressures than the patient's therapeutic pressure. In this regard, pressure from the ventilator is significantly higher than the patient's therapeutic pressure. Pressure sensing can be implemented inside the mask near the patient interface port(s), facilitating the ventilator to have a means to servo control pressure at the patient interface port(s). Having higher pressure from the ventilator and an active exhalation valve in the mask allows for the tubing size to be significantly smaller (e.g. 1-9 mm ID) compared to conventional ventilators (22 mm ID for adults/15 mm ID for pediatric). One obvious benefit of smaller tubing is that it provides less bulk for patient and/or caregivers to manage. For today's smallest ventilators, the bulk of the tubing is as significant as the bulk of the ventilator. Another benefit of the smaller tubing is that is allows for more convenient ways of affixing the mask to the patient. For instance, the tubing can go around the patient's ears to hold the mask to the face, instead of requiring straps (typically called "headgear") to affix the mask to the face. Along these lines, the discomfort, complication, and non-discrete look of the headgear is another significant factor leading to the high non-compliance rate for CPAP therapy. Another benefit to the smaller tubing is that the mask can become smaller because it does not need to interface with the large tubing. Indeed, large masks are another significant factor leading to the high non-compliance rate for CPAP therapy since, in addition to being non-discrete, they often cause claustrophobia.

The present invention is best understood by reference to the following detailed description when read in conjunction with the accompanying drawings.

BRIEF DESCRIPTION OF THE DRAWINGS

These, as well as other features of the present invention, will become more apparent upon reference to the drawings wherein.

Common reference numerals are used throughout the drawings and detailed description to indicate like elements.

DETAILED DESCRIPTION OF THE INVENTION

Figure 1:
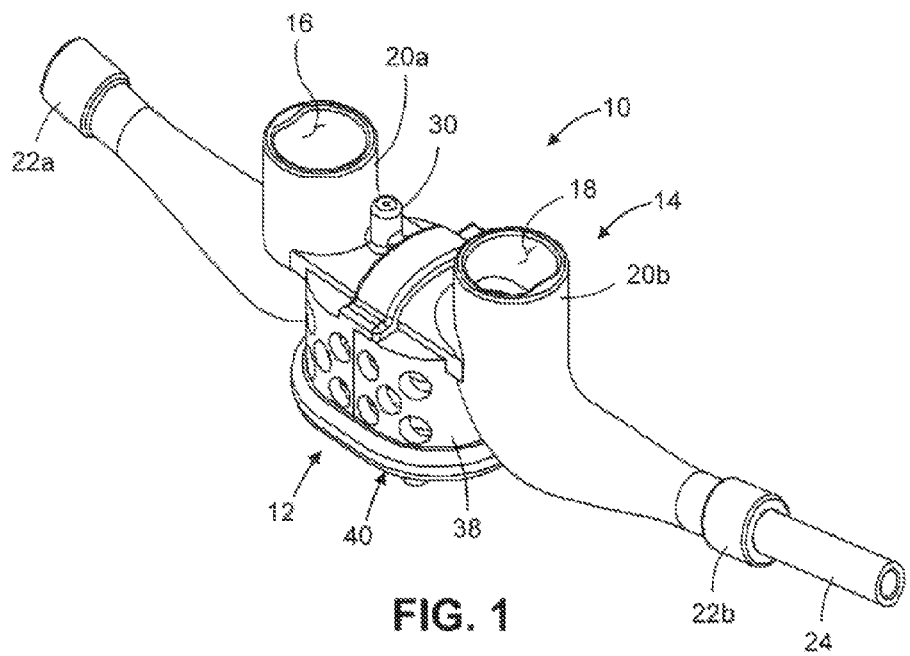
FIG. 1 is an isometric view of a nasal pillows mask constructed in accordance with a first embodiment of the present invention and including an integrated diaphragm-implementation piloted exhalation valve.
Figure 2:
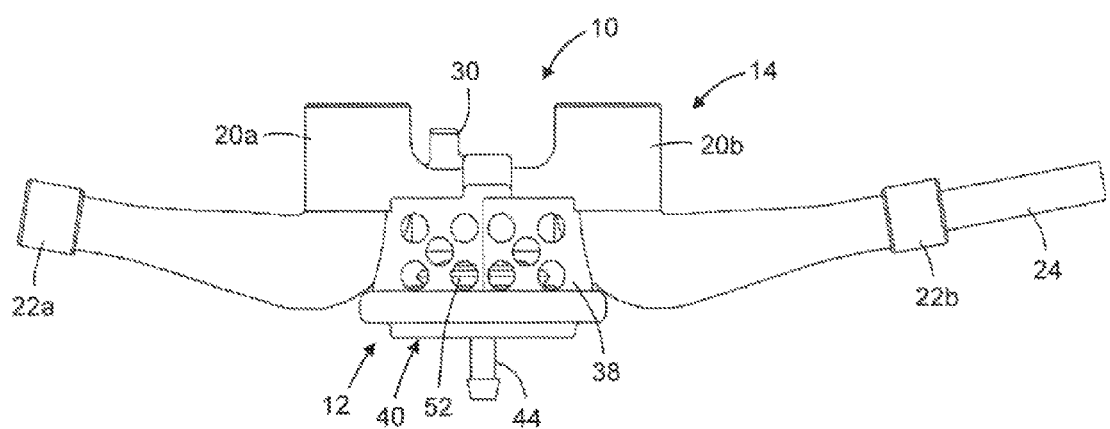
FIG. 2 is a front elevational view of the nasal pillows mask shown in FIG. 1.

Referring now to the drawings wherein the showings are for purposes of illustrating various embodiments of the present invention only, and not for purposes of limiting the same, FIGS. 1-4 depict a ventilation mask 10 constructed in accordance with a first embodiment of the present invention. The mask is depicted as a nasal prongs mask, however those skilled in the art will recognize that other ventilation masks are contemplated herein such as nasal pillows masks, nasal masks and oronasal masks and for purposes of this application the term mask and/or ventilation mask will include all such mask structures. Additionally, for purposes of this application, the term "direct nasal interface mask" will be deemed to encompass those masks which are configured to facilitate the direct introduction of therapeutic fluid pressure into the nostrils of a patent, such masks including, but not being limited to, nasal pillows masks, nasal prongs masks, and nasal cradle masks. The mask 10 includes an integrated, diaphragm-implemented, piloted exhalation valve 12, the structural and functional attributes of which will be described in more detail below.

Figure 3:
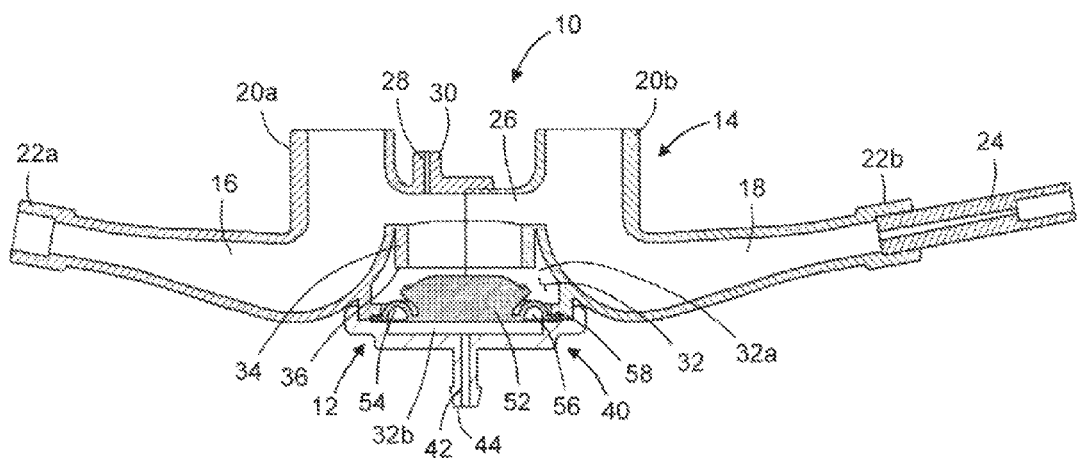
FIG. 3 is a cross-sectional view of the nasal pillows mask shown in FIG. 2.
Figure 4:
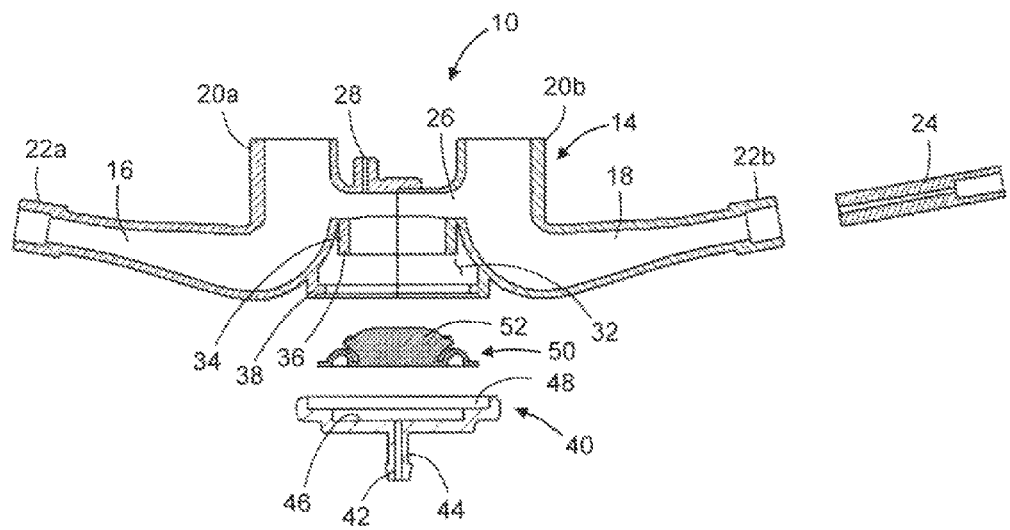
FIG. 4 is an exploded, cross-sectional front view of the nasal pillows mask shown in FIG. 3.
Figure 5:
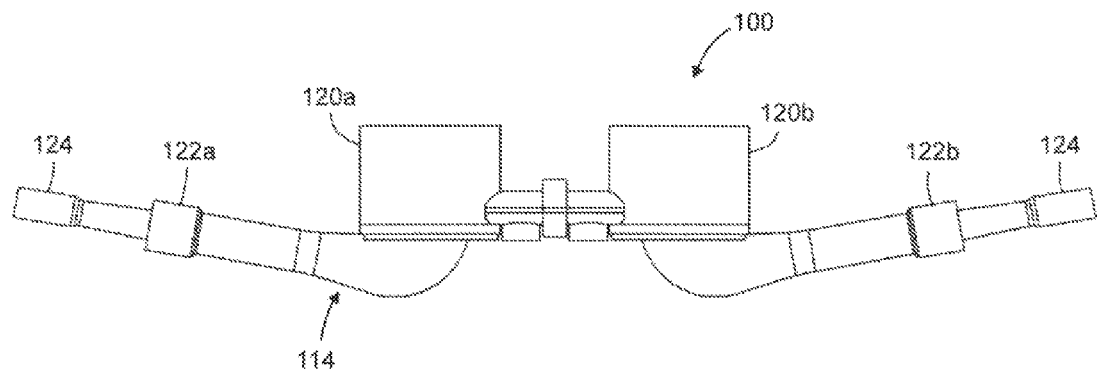
FIG. 5 is a front elevational view of a nasal pillows mask constructed in accordance with a second embodiment of the present invention and including an integrated flapper-implementation exhalation valve.

As seen in FIGS. 1-4, the mask 10 comprises a housing 14 which defines first and second fluid flow passages 16, 18. As best seen in FIGS. 3 and 4, the flow passages 16, 18 are formed within the housing 14 to have substantially identical shapes or contours. Although illustrated with a pair of flow passages, 16, 18, those skilled in the art will recognize that a single flow passage is additionally contemplated herein. In the mask 10, one end of each of the flow passages 16, 18 is defined by a respective one of an identically configured pair of generally cylindrical, tubular protrusions 20a, 20b of the housing 14. The opposite end of each of the flow passages 16, 18 is defined by a respective one of an identically configured pair of connector ports 22a, 22b of the housing 14. As seen in FIGS. 3 and 4, the connector ports 22a, 22b are each sized and configured to accommodate the advancement of a distal end portion of a tubular fluid line 24 therein. As is apparent from FIG. 3, the operative engagement of a fluid line 24 to each of the connector ports 22a, 22b effectively places such fluid lines 24 into fluid communication with respective ones of the flow passages 16, 18. In the housing 14, the spacing between the protrusions 20a, 20b is selected to facilitate the general alignment thereof with the nostrils of an adult patient when the mask 10 is worn by such patient.

In the mask 10, the flow passages 16, 18 are preferably not fluidly isolated from each other. Rather, as also seen in FIGS. 3 and 4, the housing 14 may define an optional cross passage 26 which extends between the protrusions 20a, 20b thereof, and effectively places the flow passages 16, 18 into fluid communication with each other. The cross passage 26 is further placed into fluid communication with ambient air by an optional vent port 28 which is fluidly coupled thereto. The vent port 28 is defined by and extends axially through a generally cylindrical boss 30 of the housing 14 which protrudes upwardly between the protrusions 20a, 20b thereof.

The housing 14 of the mask 10 further defines an internal valve chamber 32 which fluidly communicates with the cross passage 26. As further seen in FIGS. 3 and 4, disposed at the junction between the cross passage 26 and valve chamber 32 is a tubular projection 34 of the housing 14. The projection 34 defines an annular distal rim or seating surface 36 which is used in the operation of the valve 12 in manner which will be described in more detail below. The projection 34 protrudes into the valve chamber 32, and defines the conduit which places the valve chamber 32 into fluid communication with the cross passage 26.

As best seen in FIGS. 3 and 4, the valve chamber 32 is defined in large measure by a valve wall 38 of the housing 14 which is generally oriented between the flow passages 16, 18 thereof and, when viewed from the perspective shown in FIGS. 1-4, is disposed below the cross passage 26. As is also apparent from FIGS. 1 and 2, the valve wall 38 has a perforated construction, thus facilitating the fluid communication between the valve chamber 32 partially defined thereby and ambient air.

In the mask 10, the end of the valve chamber 32 disposed furthest from the cross passage 26 is enclosed by a valve cap 40 which may be removably attached or permanently attached to the distal portion or rim of the valve wall 38 in the manner best seen in FIG. 3. The valve cap 40 includes a pilot port 42 which, when the valve cap 40 is coupled to the valve wall 38, is placed into fluid communication with the valve chamber 32. The pilot port 42 is partially defined by and extends axially through a generally cylindrical connector 44 of the valve cap 40. As best seen in FIGS. 3 and 4, one end of the pilot port 42 is disposed within a generally planar base surface 46 defined by the valve cap 40. In addition to the base surface 46, the valve cap 40 defines a continuous shoulder 48 which, from the perspective shown in FIG. 4, is elevated above the base surface 46. This embodiment shows a pneumatically piloted diaphragm; it is additionally contemplated that the valve 12 can be driven in an electromechanical manner (e.g., with an electromagnet instead of using the above mentioned pilot port 42).

The mask 10 of the present invention further comprises a diaphragm 50 which resides within the valve chamber 32. Although various configurations of diaphragms 50 are contemplated herein, as is also best seen in FIGS. 3 and 4, the diaphragm 50 has an enlarged, central main body portion 52, and a peripheral flange portion 54 which is integrally connected to and circumvents the main body portion 52. The flange portion 54 includes an arcuately contoured central region which is oriented between the distal region thereof and the main body portion 52, and defines a continuous, generally concave channel 56. The diaphragm 50 is preferably fabricated from a suitable resilient material.

In the mask 10, the distal region of the flange portion 54 of the diaphragm 50 which is disposed outward of the arcuate central region thereof is normally captured between the valve cap 40 and the valve wall 38 when the valve cap 40 is operatively engaged to the valve wall 38. More particularly, as seen in FIG. 3, the distal region of the flange portion 54 is compressed and thus captured between the shoulder 48 of the valve cap 40 and a lip portion 58 of the valve wall 38 which protrudes inwardly from the inner surface thereof. The diaphragm 50 is preferably sized such that when the distal region of the flange portion 54 thereof is captured between the shoulder 48 and lip portion 58 in the aforementioned manner, the arcuate central region of the flange portion 54 is disposed directly adjacent the inner peripheral surface of the lip portion 58. Additionally, the channel 56 defined by the flange portion 54 is directed toward and thus faces the base surface 46 of the valve cap 40.

In the mask 10, the diaphragm 50 effectively segregates the valve chamber 32 into a patient side or region 32a, and a pilot side or region 32b. More particularly, due to the aforementioned manner in which the diaphragm 50 is captured between the valve cap 40 and the valve wall 38, the patient and pilot regions 32a, 32b of the valve chamber 32 are separated from each other by the diaphragm 50, and are of differing volumes. Along these lines, the fluid conduit defined by the projection 34 communicates directly with the patient region 32a of the valve chamber 32, while the pilot port 42 defined by the connector 44 communicates directly with the pilot region 32b of the valve chamber 32.

The diaphragm 50 (and hence the valve 12) is selectively moveable between an open position (shown in FIG. 3) and a closed position. Importantly, in either of its open or closed positions, the diaphragm 50 is not seated directly against the base surface 46 of the valve cap 40. Rather, a gap is normally maintained therebetween. As seen in FIG. 3, the width of such gap when the diaphragm 50 is in its open position is generally equal to the fixed distance separating the base surface 46 of the valve cap 40 from the shoulder 48 thereof. When the diaphragm 50 is in its open position, it is also disposed in spaced relation to the projection 34 of the housing 14, and in particular the seating surface 36 defined thereby. As such, when the diaphragm 50 is in its open position, fluid is able to freely pass between the flow passages 16, 18 and ambient air via the cross passage 26, the flow conduit defined by the projection 34, and the perforated openings within the valve wall 38 partially defining the valve chamber 32.

The diaphragm 50 may be resiliently deformable from its open position (to which it may be normally biased) to its closed position. It is an important feature of the present invention that the diaphragm 50 is normally biased in its open position which provides a fail safe to allow a patient to inhale ambient air through the valve and exhale ambient air through the valve even during any ventilator malfunction.

When moved or actuated to the closed position, the main body portion 52 of the diaphragm 50 is firmly seated against the seating surface 36 defined by the projection 34, thus effectively blocking fluid communication between the cross passage 26 (and hence the flow passages 16, 18) and the valve chamber 32. More particularly, when viewed from the perspective shown in FIG. 3, the peripheral region of the top surface of the main body portion 52 is seated against the seating surface 36, with a central region of the top surface of the main body portion 52 protruding slightly into the interior of the projection 34, i.e., the fluid conduit defined by the projection 34.

As is apparent from the foregoing description, in the mask 10, the valve 12 thereof is collectively defined by the projection 34, valve wall 38, valve cap 40 and diaphragm 50. Additionally, in the mask 10, it is contemplated that the valve 12 will be piloted, with the movement of the diaphragm 50 to the closed position as described above being facilitated by the introduction of positive fluid pressure into the gap normally defined between the diaphragm 50 and the base surface 46 via the pilot port 42, i.e., into the pilot region 32b of the valve chamber 32. In this regard, it is contemplated that during the use of the mask 10 by a patient, a pilot fluid line (not shown) from a ventilator will be coupled to the connector 44. It is also contemplated that during the inspiratory phase of the breathing cycle of the patient wearing the mask 10, the fluid pressure level introduced into the pilot region 32b of the valve chamber 32 via the pilot port 42 will be sufficient to facilitate the movement of the diaphragm 50 to its closed position. Conversely, during the expiratory phase of the breathing cycle of the patient wearing the mask 10, it is contemplated that the discontinuation of the fluid flow through the pilot port 42, coupled with the resiliency of the diaphragm 50, a biasing spring (not shown) operatively coupled to the main body portion 52 of the diaphragm 50, and/or positive pressure applied to the main body portion 52 of the diaphragm 50, will facilitate the movement of the diaphragm 50 back to the open position. As will be recognized, the movement of the diaphragm 50 to the open position allows the air exhaled from the patient to be vented to ambient air after entering the patient region 32a of the valve chamber 32 via the perforated openings of the valve wall 38 communicating with the valve chamber 32.

As will be recognized, based upon the application of pilot pressure, the diaphragm 50 travels from a fully open position through a partially open position to a fully closed position. In this regard, the diaphragm 50 will be partially open or partially closed during exhalation to maintain desired ventilation therapy. Additionally, a positive airway pressure can be controlled with any expiratory flow value by modulating the pilot pressure within the pilot region 32b of the valve chamber 32 and hence the position of the diaphragm 50. Further, when pilot pressure is discontinued to the diaphragm, the diaphragm 50 moves to an open position wherein the patient can inhale and exhale through the mask with minimal restriction and with minimal carbon dioxide retention within the mask 10. This is an important feature of the present invention which allows a patient to wear the mask 10 without ventilation therapy being applied to the mask such that the mask 10 is comfortable to wear and can be worn without carbon dioxide buildup. This feature is highly advantageous for the treatment of obstructive sleep apnea where patients complain of discomfort with ventilation therapy due to mask and pressure discomfort. When it is detected that a patient requires sleep apnea therapy, the ventilation therapy can be started (i.e., in an obstructive sleep apnea situation).

In this regard, the present invention contemplates a method of ventilation utilizing a mask wherein patient inhalation and patient exhalation is facilitated through the mask to ambient air when the ventilator is not delivering a therapeutic level of pressure. For instance, additional valving in the mask may be implemented for this purpose. Since the mask does not facilitate CO2 buildup, the ventilator can remain off while the mask is worn by the patient and ventilation therapy can be initiated upon sensing or detecting a patient requirement, such as sleep apnea therapy, by conventional sensors incorporated into the mask and ventilator. In this regard, conventional ventilators can be readily modified via conventional software changes to allow the mask to be worn without supplying pressure to the mask unless and until a patient requirement is sensed and subsequently communicated to the ventilator to provide necessary ventilation to the patient. Such modification may additionally require the use of a conventional check valve to ensure that patient exhalation is facilitated through the exhalation valve on the mask and not back into the ventilator delivery circuit.

As indicated above, in the embodiment shown in FIGS. 1-4, the diaphragm 50 is pneumatically piloted, with the position thereof being regulated by selectively modulating the pilot pressure within the pilot region 32b of the valve chamber 32. However, it is contemplated that alternative modalities, such as an electromagnetic actuator, can be used to drive the valve 12. For example, as also indicated above, in an alternative embodiment, the valve 12 may be driven in an electromechanical manner through the use of an electromagnet instead of using the above-described pilot port 42.

As indicated above, in the mask 10, the valve cap 40 is releasably attached to the valve wall 38 of the housing 14. As a result, the selective detachment of the valve cap 40 from the housing 14 allows for the removal of the diaphragm 50 from within the valve chamber 32 as permits the periodic cleaning or disinfection thereof. In addition, the detachment of the valve cap 40 from the valve wall 38 of the housing 14 also permits access to and the cleaning or disinfection of the interior surfaces of the valve chamber 32. Port 28 provides a means for pressure measurement inside the mask, and thus may optionally serve as a pressure sensing port.

Referring now to FIGS. 5-9, there is shown a nasal pillows mask 100 constructed in accordance with a second embodiment of the present invention. The mask 100 includes an integrated, flapper-implemented exhalation valve 112, the structural and functional attributes of which will be described in more detail below.

Figure 8:
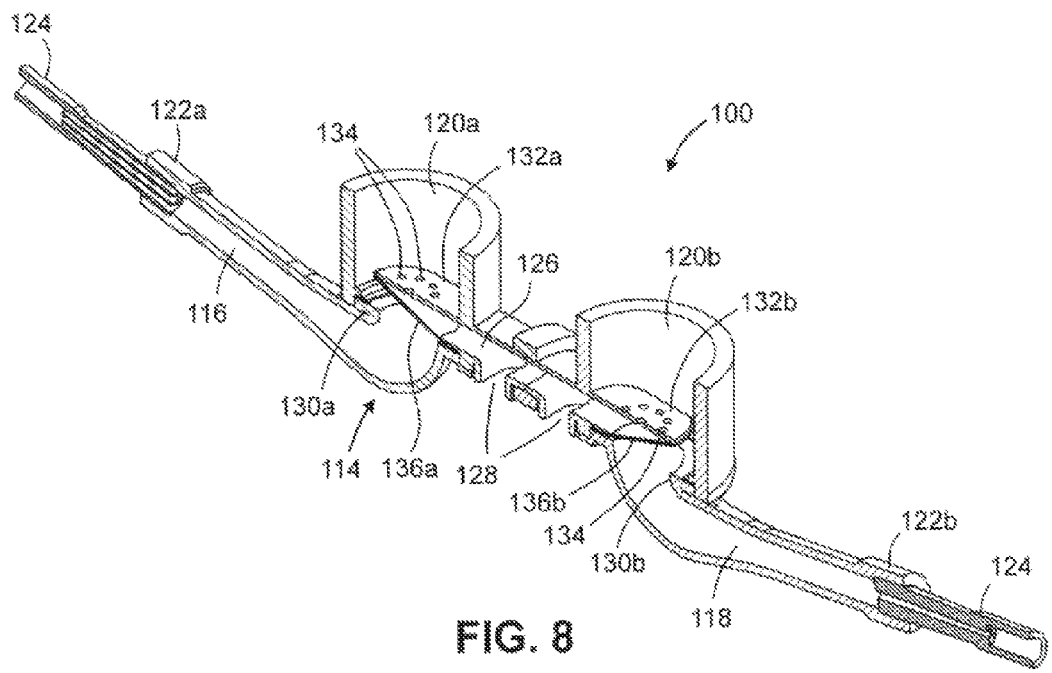
FIG. 8 is a cross-sectional, isometric view of the nasal pillows mask shown in FIG. 5.
Figure 9:
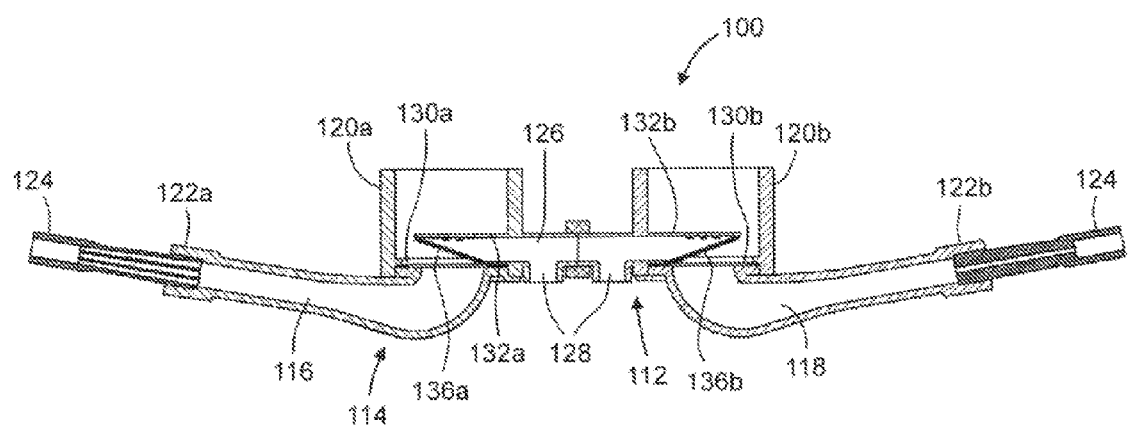
FIG. 9 is a cross-sectional view of the nasal pillows mask shown in FIG. 5.

As seen in FIGS. 5-9, the mask 100 comprises a housing 114 which defines first and second fluid flow passages 116, 118. As seen in FIGS. 8 and 9, the flow passages 116, 118 are formed within the housing 114 to have substantially identical shapes or contours. As with the first embodiment of this invention, a single flow passage is additionally expressly contemplated herein. In the mask 100, one end of each of the flow passages 116, 118 is defined by a respective one of an identically configured pair of generally cylindrical, tubular protrusions 120a, 120b of the housing 114. The opposite end of each of the flow passages 116, 118 is defined by a respective one of an identically configured pair of connector ports 122a, 122b of the housing 114. The connector ports 122a, 122b are each sized and configured to accommodate the advancement and frictional retention of a distal end portion of a tubular fluid line 124 therein. As most apparent from FIGS. 8 and 9, the operative engagement of a fluid line 124 to each of the connector portions 122a, 122b effectively places such fluid lines 124 into fluid communication with respective ones of the flow passages 116, 118. In the housing 114, the spacing between the protrusions 120a, 120b is selected to facilitate the general alignment thereof with the nostrils of an adult patient when the mask 100 is worn by such patient.

In the mask 100, the flow passages 116, 118 are not fluidly isolated from each other. Rather, as seen in FIGS. 8 and 9, the housing 114 further defines an optional cross passage 126 which extends between the protrusions 120a, 120b thereof, and effectively places the flow passages 116, 118 into fluid communication with each other. The cross passage 126 is further placed into communication with ambient air by an identically configured pair of vent ports 128 which are fluidly coupled thereto. The vent ports 128, which are disposed in side-by-side, spaced relation to each other, are formed within the housing 14 between the protrusions 120a, 120b thereof and, when viewed from the perspective shown in FIG. 9, face downwardly in a direction opposite that of the open distal ends of the protrusions 120a, 120b.

As is best seen in FIGS. 8 and 9, the protrusions 120a, 120b are preferably formed as separate and distinct components or sections of the housing 114 which, when mated to the remainder thereof, facilitate the formation of an identically configured pair of arcuate, semi-circular shoulders 130a, 130b. The shoulders 130a, 130b defined by the housing 114 are located within the interiors of respective ones of the protrusions 120a, 120b thereof. More particularly, each shoulder 130a, 130b is formed in close proximity to that end of the corresponding protrusion 120a, 120b disposed furthest from the open distal end thereof. The use of the shoulders 130a, 130b will be described in more detail below.

Figure 6:
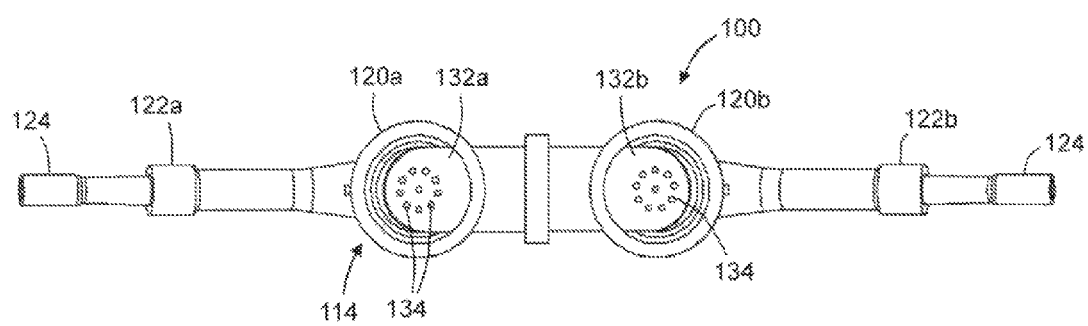
FIG. 6 is a top plan view of the nasal pillows mask shown in FIG. 5.
Figure 7:
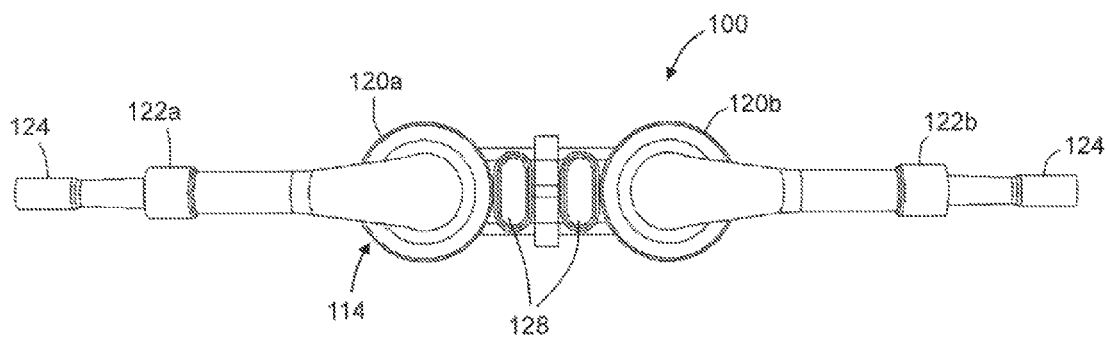
FIG. 7 is a bottom plan view of the nasal pillows mask shown in FIG. 5.

In the mask 100, the cross passage 126 is partially defined by one or more valve projections 132a, 132b of the housing 114 which are integrally connected to respective ones of the protrusions 120a, 120b, and protrude generally perpendicularly from the inner surfaces thereof in opposed relation to each other. As seen in FIGS. 6, 8, and 9, the valve projections 132a, 132b are not sized to completely span or cover those portions of the flow passages 116, 118 defined by the protrusions 120a, 120b. Rather, each of the valve projections 132a, 132b is formed to define an arcuate peripheral edge segment, and sized such that the arcuate peripheral edge segment thereof is separated or spaced from the inner surface of the corresponding protrusion 120a, 120b by a gap which is of a prescribed width. Further, as seen in FIGS. 6 and 8, each of the valve projections 132a, 132b preferably includes a plurality of flow openings 134 disposed therein in a generally circular pattern. The flow openings 134 of the valve projections 132a, 132b each fluidly communicate with the cross passage 126, and are used for purposed which will also be described in more detail below.

The mask 100 of the present invention further comprises a flapper, which is preferably segregated into an identically configured pair of flapper segments 136a, 136b. The flapper segments 136a, 136b are each preferably fabricated from a suitable, resilient material. As seen in FIGS. 8 and 9, the flapper segments 136a, 136b reside within the interiors of respective ones of the protrusions 120a, 120b. Additionally, when viewed from the perspective shown in FIGS. 8 and 9, an inner end portion of each of the flapper segments 136a, 136b is firmly secured to the housing 114 as a result of being captured between prescribed components or sections thereof. However, those portions of the flapper segments 136a, 136b not rigidly secured to the housing 114 are free to resiliently move relative thereto, in a manner which will be described in more detail below.

The flapper segments 136a, 136b (and hence the valve 112) are selectively moveable between a closed position (shown in FIGS. 8 and 9) and an open position. When the flapper segments 136a, 136b are each in the open position, that portion of the peripheral edge thereof not secured to the housing 114 (i.e., not captured between separate sections of the housing 114) is normally seated against a corresponding one of the shoulders 130a, 130b. As a result, any fluid (e.g., air exhaled from the nose of a patient wearing the mask) flowing into the flow passages 116, 118 via the open distal ends of the protrusions 120a, 120b is vented to ambient air via the cross passage 126 and vent ports 128. In this regard, such fluid is able to enter the cross passage 126 through the gaps defined between the valve projections 132a, 132b and inner surfaces of the corresponding protrusions 120a, 120b.

The flapper segments 136a, 136b may be resiliently deformable from the open position described above (to which they are normally biased) to the closed position shown in FIGS. 8 and 9. More particularly, when moved or actuated to the closed position, those portions of the flapper segments 136a, 136b not secured to the housing 114 are effectively placed into sealed contact with peripheral portions of respective ones of the valve projections 132a, 132b in a manner substantially covering or obstructing the opposed ends of the cross passage 126 fluidly communicating the flow passages 116, 118. However, even when the flapper segments 136a, 136b are in the closed position, some measure of fluid may still be vented from the flow passages 116, 118 to ambient air by entering the cross passage 126 via the flow openings 134 included in each of the valve projections 132a, 132b.

As is apparent from the foregoing description, in the mask 100, the valve 112 thereof is collectively defined by the shoulders 130a, 130b, valve projections 132a, 132b, and flapper segments 136a, 136b of the flapper. Additionally, in the mask 100, it is contemplated that the flapper segments 136a, 136b will normally be biased to the open position. In this regard, it is contemplated that during the inspiratory phase of the breathing cycle of a patient using the mask 100, positive fluid pressure introduced into the flow passages 116, 118 by a ventilator fluidly coupled thereto via the fluid lines 124 will act against the flapper segments 136a, 136b in a manner facilitating the movement of such flapper segments 136a, 136b from their normally open position, to the closed position shown in FIGS. 8 and 9. As a result, fluid is able to flow freely through the flow passages 116, 118 into the patient's nostrils, and is substantially prevented from being vented to ambient air via the cross passage 126, except for a small portion of flow that passes through flow openings 134. This small flow through flow openings 134 provides for a means to bleed off pressure and therefore more easily control the valve.

Conversely, during the expiratory phase of the breathing cycle of the patient wearing the mask 100, it is contemplated that a reduction in the fluid pressure level introduced into the flow passages 116, 118 from the fluid lines 124 to below a prescribed level will allow the flapper segments 136*a*, 136*b* to resiliently return to their normal, open positions engaging respective ones of the shoulders 130*a*, 130*b*. When the flapper segments 136*a*, 136*b* return to their open positions, air exhaled from the patient's nostrils during the expiratory phase of the patient's breathing circuit is vented to ambient air via the cross passage 126 and vent ports 128. In this regard, though the movement of the flapper segments 136*a*, 136*b* to the open positions effectively blocks those portions of the flow passages 116, 118, air exhaled from the patient is able to flow through the gaps defined between the valve projections 132*a*, 132*b* and the inner surfaces of the protrusions 120*a*, 120*b*, and hence into the opposed open ends of the cross passage 126.

Advantageously, the mask 100 constructed in accordance with the present invention has a total flow requirement which is much lower in comparison to that of a traditional vented PAP mask. This provides the mask 100 with several advantages, including: reduced flow from the ventilator, and thus the ability to use smaller tubes; a reduction in the conducted noise from the ventilator to ambient air through the open vent ports 128 in the mask 100; a reduction in oxygen consumption when required with the PAP therapy due to lower flow requirements; and a reduction in water consumption of a humidifier due to lower flow requirements.

This disclosure provides exemplary embodiments of the present invention. The scope of the present invention is not limited by these exemplary embodiments. Numerous variations, whether explicitly provided for by the specification or implied by the specification, such as variations in structure, dimension, type of material and manufacturing process may be implemented by one of skill in the art in view of this disclosure.

What is claimed is:

1. A method of ventilating a patient utilizing a direct nasal interface mask worn by the patient and fluidly connected to a ventilator adapted to supply a pressurized, breathable gas to the direct nasal interface mask, the method comprising the steps of:
   a) providing the direct nasal interface mask with a housing defining at least one flow passage, and a piloted exhalation valve is integrated into the housing and fluidly coupled to the flow passage; and
   b) applying a pilot pressure to the exhalation valve via the ventilator and in a manner which facilitates the selective movement thereof from an open position to which it is normally biased and wherein at least a portion of the flow passage is vented to ambient air, to a closed position wherein fluid flow between the flow passage and ambient air is at least partially obstructed thereby.

2. The method of claim 1 wherein step (a) comprises configuring the exhalation valve to completely obstruct fluid flow between the flow passage and ambient air when moved to the closed position in step (b).

3. The method of claim 1 wherein step (a) comprises configuring the exhalation valve to vent the entirety of the flow passage to ambient air when moved to the open position in step (b).

4. The method of claim 1 wherein step (a) comprises configuring the exhalation valve to adjust fluid flow between the flow passage and ambient air when disposed between the closed position and open position in step (b).

5. The method of claim 1 wherein step (a) comprises configuring the housing to include a pressure sensing port, and step (b) comprises sensing pressure within the flow passage through the use of the pressure sensing port to facilitate at least one of achieving and monitoring a therapeutic pressure level therein.

6. The method of claim 1 wherein step (a) comprises configuring the exhalation valve to include a diaphragm which is movable between the closed and open positions in step (b).

7. The method of claim 1 wherein step (a) comprises configuring the exhalation valve to include at least one flapper which is movable between the closed and open positions in step (b).

8. The method of claim 1 wherein step (b) comprises initially supplying no pressurized, breathable gas from the ventilator to the patient via the direct nasal interface mask.

9. The method of claim 8 further comprising the step of:
   c) initiating the delivery of the pressurized, breathable gas from the ventilator to the patient at a prescribed therapeutic pressure level upon an occurrence of a predetermined event.

10. The method of claim 9 wherein the predetermined event of step (c) is at least one of:
    an elapse of a set time interval;
    a detection of a patient breathing pattern indicative of an airway obstruction in the patient; and
    a detection of a patient breathing pattern indicative of the patient falling asleep.

11. A method of ventilating a patient using a direct nasal interface mask worn by the patient and fluidly connected to a ventilator adapted to supply a pressurized, breathable gas to the direct nasal interface mask, the method comprising the steps of:
    a) providing the direct nasal interface mask with a housing at least partially defining a valve chamber which fluidly communicates with ambient air, a pilot port which fluidly communicates with the valve chamber, at least one flow passage which is selectively placeable into fluid communication with the valve chamber, and a diaphragm which is disposed within the valve chamber and selectively movable from an open position to which it is normally biased and wherein the flow passage is vented to ambient air via the valve chamber, to a closed position wherein fluid flow between the flow passage and the valve chamber is obstructed thereby; and
    b) using the pilot port to selectively apply a pilot pressure from the ventilator to the diaphragm in a manner facilitating the movement thereof to the closed position.

12. The method of claim 11 wherein step (a) comprises configuring the housing to include a pressure sensing port which fluidly communicates with the flow passage, and step (b) comprises sensing pressure within the flow passage through the use of the pressure sensing port to facilitate at least one of achieving and monitoring a therapeutic pressure level therein.

13. The method of claim 11 wherein step (b) further comprises initially supplying no pressurized, breathable gas from the ventilator to the patient via the direct nasal interface mask, and initially supplying no pilot pressure from the ventilator to the diaphragm.

14. The method of claim 13 further comprising the step of:
- c) initiating the delivery of the pressurized, breathable gas from the ventilator to the patient at a prescribed therapeutic pressure level upon an occurrence of a predetermined event.

15. The method of claim 14 wherein the predetermined event of step (c) is at least one of:
- (i) an elapse of a set time interval;
- (ii) a detection of a patient breathing pattern indicative of an airway obstruction in the patient; and
- (iii) a detection of a patient breathing pattern indicative of the patient falling asleep.

16. The method of claim 13 further comprising the steps of:
- c) initiating the delivery of the pressurized, breathable gas from the ventilator to the direct nasal interface mask through the use of tubing having an inner diameter in the range of from about 1 mm to about 9 mm; and
- d) delivering the pressurized, breathable gas from the ventilator to the direct nasal interface mask through the tubing at a delivery pressure level which exceeds a prescribed therapeutic pressure level for the delivery of the pressurized, breathable gas from the direct nasal interface mask to the patient.

\* \* \* \* \*